United States Patent
Ho et al.

(10) Patent No.: US 9,609,670 B2
(45) Date of Patent: Mar. 28, 2017

(54) ADDRESS SPACE PARTITIONING AND FILTERING FOR DISCRETIONARY WIRELESS CONNECTION RESPONSE

(71) Applicant: TEXAS INSTRUMENTS INCORPORATED, Dallas, TX (US)

(72) Inventors: Jin-Meng Ho, Plano, TX (US); June Chul Roh, Allen, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 136 days.

(21) Appl. No.: 14/520,793

(22) Filed: Oct. 22, 2014

(65) Prior Publication Data
US 2015/0038187 A1   Feb. 5, 2015

Related U.S. Application Data

(63) Continuation of application No. 12/963,942, filed on Dec. 9, 2010, now Pat. No. 8,897,217.

(60) Provisional application No. 61/285,043, filed on Dec. 9, 2009.

(51) Int. Cl.

| | |
|---|---|
| H04W 40/00 | (2009.01) |
| H04B 7/00 | (2006.01) |
| H04W 24/10 | (2009.01) |
| H04Q 7/20 | (2006.01) |
| H04W 8/02 | (2009.01) |
| G08B 23/00 | (2006.01) |
| A61N 1/372 | (2006.01) |
| H04W 76/02 | (2009.01) |
| H04W 72/04 | (2009.01) |

(52) U.S. Cl.
CPC ........ *H04W 76/02* (2013.01); *A61N 1/37252* (2013.01); *H04W 72/04* (2013.01)

(58) Field of Classification Search
CPC ...... H04W 48/02; H04W 48/08; H04W 48/16
USPC ........ 340/502, 501; 370/384, 252, 350, 461, 370/431, 456, 450, 459; 455/432.1, 433
See application file for complete search history.

(56) References Cited

U.S. PATENT DOCUMENTS

| | | | |
|---|---|---|---|
| 7,552,255 B1 | 6/2009 | George et al. | |
| 7,787,946 B2 * | 8/2010 | Stahmann | A61B 5/0031 607/3 |
| 8,745,409 B2 * | 6/2014 | Teicher | G06F 21/78 705/34 |

(Continued)

*Primary Examiner* — Wutchung Chu
(74) *Attorney, Agent, or Firm* — Tuenlap D. Chan; Charles A. Brill; Frank D. Cimino

(57) ABSTRACT

A system and method for providing wireless communications between a medical controller hub and an implant node are disclosed. The hub transmits signals to facilitate communication connections with the node. The signals include connection invitation polls with identification parameters. A node monitors the hub's transmissions for the connection invitation polls. When a poll is detected, the node compares the identification parameters to a list of preferred identification values. If the received identification parameter is on the preferred list, and the node and hub are not already connected, then the node responds to the connection invitation poll. If the received identification parameter is not on the preferred list, then the node continues to monitor hub transmissions for other connection invitation polls that include identification parameters that are on the preferred list.

6 Claims, 2 Drawing Sheets

(56) References Cited

U.S. PATENT DOCUMENTS

| | | | |
|---|---|---|---|
| 8,979,756 B2* | 3/2015 | Alsafadi | A61B 5/0002 |
| | | | 600/300 |
| 9,218,454 B2* | 12/2015 | Kiani | G06F 19/327 |
| 2002/0026384 A1 | 2/2002 | Imanaka et al. | |
| 2002/0036991 A1 | 3/2002 | Inoue | |
| 2002/0123673 A1 | 9/2002 | Webb et al. | |
| 2002/0184539 A1 | 12/2002 | Fukuda et al. | |
| 2005/0096035 A1* | 5/2005 | Haberman | H04W 4/00 |
| | | | 455/422.1 |
| 2006/0224048 A1* | 10/2006 | Devaul | A61B 5/0024 |
| | | | 600/300 |
| 2008/0044014 A1* | 2/2008 | Corndorf | H04L 63/12 |
| | | | 380/37 |
| 2008/0058900 A1 | 3/2008 | Berthelsdorf et al. | |
| 2008/0198811 A1* | 8/2008 | Deshpande | H04W 48/16 |
| | | | 370/332 |
| 2009/0023391 A1 | 1/2009 | Falck | |
| 2009/0058635 A1 | 3/2009 | LaLonde et al. | |
| 2009/0069642 A1 | 3/2009 | Gao et al. | |
| 2009/0198733 A1* | 8/2009 | Gounares | G06F 19/327 |
| 2010/0191088 A1* | 7/2010 | Anderson | A61B 17/7074 |
| | | | 600/373 |
| 2012/0051314 A1 | 3/2012 | Goyal et al. | |
| 2012/0063389 A1 | 3/2012 | Abedi | |
| 2014/0136624 A1* | 5/2014 | Abhyanker | G06Q 50/01 |
| | | | 709/204 |

\* cited by examiner

ADDRESS SPACE PARTITIONING AND FILTERING FOR DISCRETIONARY WIRELESS CONNECTION RESPONSE

CROSS-REFERENCE TO RELATED APPLICATIONS

This application is a continuation of application Ser. No. 12/963,942, filed Dec. 9, 2010, which claims the benefit of U.S. Provisional Application No. 61/285,043, filed Dec. 9, 2009, the entireties of all of which are hereby incorporated by reference.

TECHNICAL FIELD

Embodiments of the invention are directed, in general, to wireless medical systems and, more specifically, to schemes used by an implant node to identify controller hubs in the Medical Implant Communications Service (MICS) band and Medical Data Services (MEDS) band.

BACKGROUND

A MICS/MEDS based system includes at least a medical controller, also known as hub, and a medical implant, also known as node, operating in the MICS band 402-405 MHz or the MEDS band 401-402 MHz and 405-406 MHz. The medical implant is located inside the body of a living organism and the medical controller is, in most cases, externally located. Medical devices may be implanted within the human body for medical diagnosis and treatment. These medical implants are miniaturized devices that typically operate as sensors or stimulators. Because it is located within a patient's body, it is impractical for a doctor, medical professional, technician, or monitoring and control device to communicate by direct, physical connection with the implant. Instead, wireless communications are used to establish links between the implant and external equipment and medical professionals. The wireless communications provide fast and reliable data exchange with the implant without requiring a direct physical connection to the patient, which allows the patient more freedom and less discomfort. External monitoring and control equipment may communicate with the implant at the patient's home, in a doctor's office, in a hospital, or at other locations. The power consumption by the transceiver forms a significant portion of the overall power consumption in the medical implant. Hence, it is desired to maximize efficiency of the medical implant transceiver to increase lifetime of the medical implant.

The location of the implanted medical device makes power consumption a critical parameter. The implant may be powered by an internal battery that is recharged periodically, such as by inductive radio frequency (RF) links. In other embodiments, medical regulations may require surgical replacement of an implant device that has low battery power, which makes low-power operation of the node a critical factor. It is important to achieve a balance between low power consumption of the implant and high quality wireless communication between the implant and external equipment. It is often not practical or even possible to reduce power consumption by simply minimizing the frequency with which the implant and external equipment communicate. Many implants require the capability to send and/or receive information with the external equipment with minimal delay at any time. For example, at any time, conditions may arise that require an implanted stimulator to change operating parameters, or an implanted sensor may need to report a critical or emergency condition. However, it is not acceptable for the implant to maintain a continuous wireless link to the external equipment because of the power required to maintain such a connection and the subsequent drain on the implant's battery or power supply.

The power consumption in the medical implant is dominated by the search for communication with an external controller in both an unconnected state and a connected state of the medical implant. In the unconnected state, the medical implant wakes up periodically, such as every few seconds, and listens for a signal for connection with an external controller. In a connected state, the medical implant follows a procedure similar to that for the unconnected state, and wakes up periodically, which may be every few seconds, and listens for the external controller with which it has connected. In one example, the medical implant in a connected state follows the procedure because the medical implant needs to detect another medical controller. For example, if the medical implant is initially connected with a medical controller at home, but the living organism containing the medical implant travels to a doctor's office, then the medical implant needs to detect and connect with the medical controller at the doctor's office. Hence the medical implant wakes up periodically, even when the medical implant is already connected with a medical controller, to detect other medical controllers. However, waking up in the connected state with a periodicity similar to that of the unconnected state leads to power wastage when the medical implant has to search for signals that typically have low strength. As the time for which the medical implant has to listen for low-strength signals increases, more power is consumed.

Communications between a controller (or "hub") and an implant (or "node") are subject to stringent regulatory restrictions. In particular, the hub often has to switch to a new operating channel selected from the ten channels total in the MICS band. The node then needs to discover that new operating channel to communicate with the hub. A node cannot normally initiate a transmission to the hub, unless in an "implant report event" (i.e., medical emergency). Furthermore, the node cannot choose the operating channel to use in an emergency, but instead the node must discover the hub's current operating channel to report the emergency. Existing solutions are either not power efficient or not in compliance with the FCC requirements for the MICS band. There is a need for a new technique for supporting power-efficient communications between implants and controllers.

SUMMARY OF THE INVENTION

Embodiments of the invention reduce the power consumption of wireless implants by allowing the implant to intelligently identify external controllers and to evaluate whether to connect with them. This allows the implant to minimize the power required during frequent wakeups for discovery of, and connection with, desired controllers.

Embodiments of the invention dramatically reduce power consumption of wireless implants, especially during their frequent wakeups for connection with an external controller (hub).

An implant needs to scan for an external hub frequently (on the order of every 2 seconds) so that it can promptly connect with a hub in case such a connected is warranted, such as when the patient wearing the implant is having a medical emergency or visiting a medical doctor. However, an implant is likely to be in the radio range of an "alien" hub with which it has nothing relevant to do but could engage in power-hungry message exchanges for a connection. To avoid unwanted connections with alien hubs and hence preserve battery power, an implant should respond to polls (connection invitation messages) from, and make a new connection with, only some specially designated hubs as enabled through our following solution.

Scheme 1: Partition the Hub ID (HID) space into three subsets. Subset 1 consists of only one special value, such as "0", which is used by emergency hubs only (i.e., those hubs that handle medical emergencies). Subset 2 is given an HID value range, such as [1, 4095], for medical doctors' hubs (i.e., those hubs operating at medical doctors' offices). Subset 3 is the remaining values of the HID space, which are made available to hubs set up at patients' homes.

An implant will be provided with the following HID values through connection with a trusted hub: the HID value from subset 1, one or more HID values from subset 2 that are used for the hubs at the offices of the doctors the patient wearing the implant is likely to visit, and the HID of the patient's home hub.

The implant will wake up as frequently as appropriate to receive connection invitation polls for a needed connection with a relevant hub. However, it will transmit a response for a connection with the hub sending the invitation only after it received a poll with the HID field set to one of the HID values with which it was last provided. If the implant received a poll from its home hub as identified with its home HID value but is still connected with the hub, it does not respond to connection invitation polls from the hub.

Scheme 2: All hubs for emergency or visiting patients will have the HID field of their connection invitation messages set to a special value, such as "0", and the HID field of their other messages set to a different value. Other hubs will never have the HID field of their messages set to that special value.

All implants will be provided with this special value, either hardcoded at the time of their manufacturing or configured through a trusted hub.

An implant will wake up as frequently as appropriate to receive connection invitation polls for a needed connection with a relevant hub. However, it will transmit a request for a connection with the hub sending the invitation only after it received a poll with the HID field set to the preset special value or it home HID value. Nevertheless, if the implant is currently connected with its home hub, it will not respond to connection invitation polls from the hub.

BRIEF DESCRIPTION OF THE DRAWINGS

Figure 1:
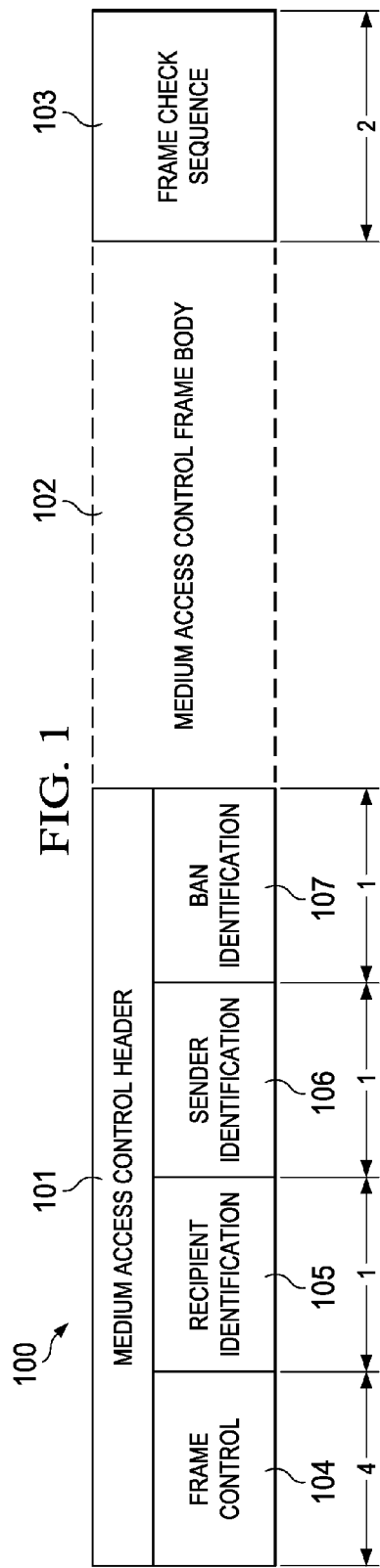
Figure 2:
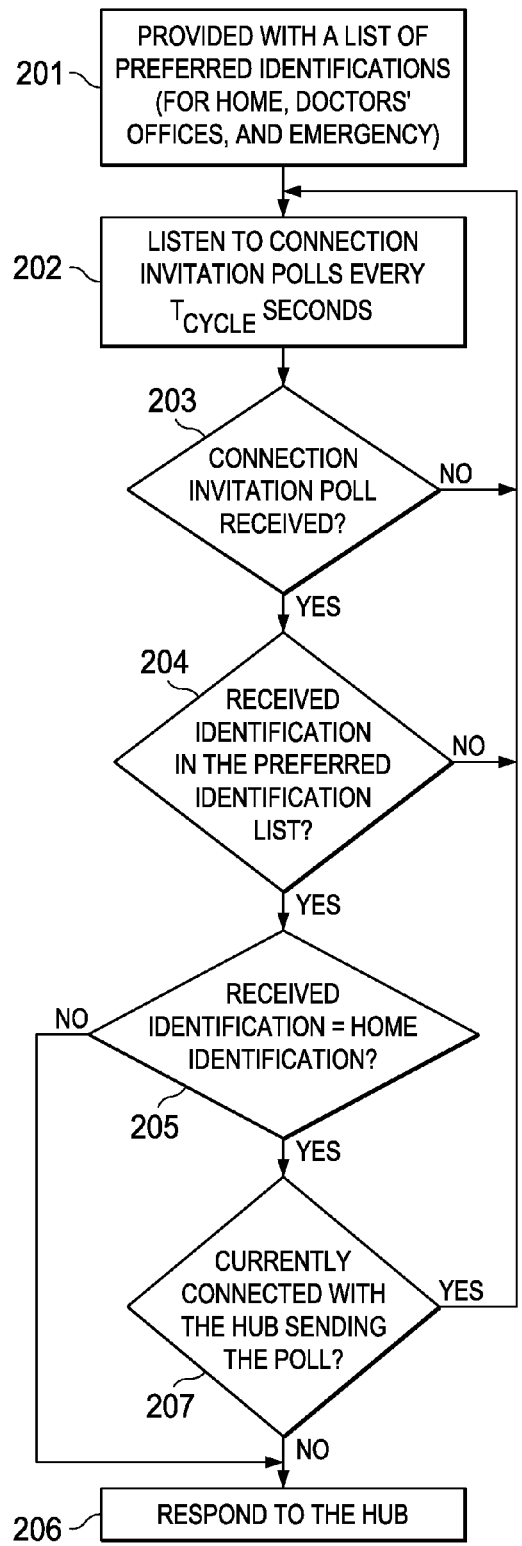

Having thus described the invention in general terms, reference will now be made to the accompanying drawings, wherein:

FIG. 1 illustrates a Medium Access Control (MAC) frame used in an exemplary embodiment;

FIG. 2 is a flowchart illustrative of an embodiment; and

Figure 3:
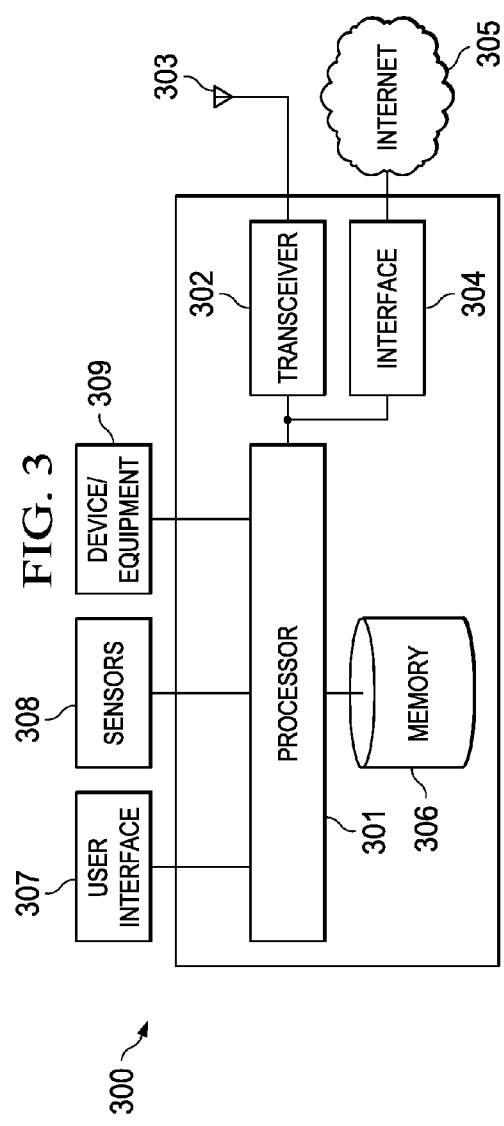

FIG. 3 is a block diagram of an exemplary embodiment of a device implementing embodiments of the invention.

DETAILED DESCRIPTION

The invention now will be described more fully hereinafter with reference to the accompanying drawings. This invention may, however, be embodied in many different forms and should not be construed as limited to the embodiments set forth herein. Rather, these embodiments are provided so that this disclosure will be thorough and complete, and will fully convey the scope of the invention to those skilled in the art. One skilled in the art may be able to use the various embodiments of the invention.

Instead of maintaining a constant wireless communication link with an external device, such as control or monitoring equipment, an implant will typically alternate between an inactive or sleep state and an active state. This allows the implant to save power during the sleep state, but requires the implant to use power following each sleep state to discover and connect with an external device. For simplification, the implant is referred to herein as a "node," and the external equipment or controller is referred to herein as a "hub." To discover the hub following a sleep state, the node may sequentially monitor a series of frequencies until it detects wakeup or poll frames broadcast by a hub. Then the node may follow a preset procedure to connect with the detected hub. Examples of hub discovery and node connection methods are disclosed in pending U.S. patent application Ser. No. 12/856,167, titled "Implant Access in the Medical Implant Communications Service Band," and filed on Aug. 13, 2010, the disclosure of which is hereby incorporated by reference herein in its entirety. The operation of a Body Area Network, including the transmission of wakeup frames and poll frames from a hub to a node, is described in the publication IEEE P802.15.6/D01, titled "Draft Standard for Body Area Network," published May 2010 by the Institute of Electrical and Electronics Engineers, Inc.

The implant node needs to frequently scan for hub transmissions so that it can promptly connect with a hub in case such a connected is warranted, such as when the patient wearing the implant is having a medical emergency or visiting a medical doctor. Typically, such scanning is performed by the node on the order of once every two seconds. When the patient is home, at his or her doctor, or at a hospital, the implant node is likely to discover and connect with a hub that is relevant to the patient and the node. On occasion, an implant node will be in radio range of an "alien" hub for which it has nothing in common and that is not relevant to the operation or monitoring of the implant node. However, upon detection of the unrelated hub, existing nodes must engage in message exchanges with the unrelated hub to establish a connection. It is a waste of power for the node to perform the connection process with an unrelated hub.

To avoid unwanted connections with alien hubs, an implant node should identify whether the discovered hub transmissions correspond to hubs of interest to the node. If the hub is part of a preselected group, the node will respond to polls messages or connection invitation messages from the hub and will make a new connection with the specially designated hub. In this manner, the node preserves battery power by not wasting power to perform a connection process with unrelated hubs.

FIG. 1 illustrates a Medium Access Control (MAC) frame 100. The MAC frame consists of a fixed-length MAC Header 101, a variable-length MAC Frame Body 102, and a fixed length Frame Check Sequence (FCS) field 103. MAC Header 101 is comprised of Frame Control field 104, Recipient ID 105, Sender ID 106, and Body Area Network (BAN) ID 107.

When a node "wakes up" from a sleep state, it listens for wakeup or poll frames transmitted by a hub. A hub may transmit wakeup or poll frames that are directed to a specific node or group of nodes or to all nodes. The hub sets the Recipient ID field 105 as appropriate in the wakeup or poll frames for the intended recipient or recipients.

In one embodiment, the hub sets the values of the Sender ID field 106 and BAN ID field 107 to indicate to recipient nodes what type of hub is transmitting. The Sender ID field 106 and BAN ID field 107 may be set to indicate broad hub classifications, such as whether the hub belongs to a patient's home, a doctor's office, or a medical facility. The values used for the Sender ID field 106 and BAN ID field 107 may be partition into three subsets, for example. In one embodiment, the subsets are related to emergency hubs, medical facility hubs, and patient home hubs.

Subset 1 consists of one special value, such as "0," which is used by emergency hubs only. The emergency hubs are configured specifically to handle medical emergencies related to implant devices. The emergency hubs transmit wakeup or poll frames that contain all zero values in the Sender ID field 106 and BAN ID field 107. When a node observes the special value in the Sender ID and BAN ID, the node knows that it has discovered an emergency hub. The node can then determine whether it should connect with the emergency hub based upon the current condition of the implant. If the node is in an emergency condition, it would connect with the emergency hub. However, if the node is not in an emergency condition, then it would not be power efficient to connect with the emergency hub since that hub is unlikely to be configured to monitor or support the patient's implant in a non-emergency condition. The non-emergency node can either return to a sleep state or may continue scanning or monitoring for a non-emergency hub.

It will be understood that more than one "special value" may be designated for emergency hubs. For example, in one embodiment, a first special value is designated for emergency hubs configured to service implants that are sensors, and a second special value is designated for emergency hubs that are configured to service implants that are stimulators. Alternatively, in other embodiments, the emergency hub special values may be based upon a hub or implant manufacturer identity, an implant type, a patient demographic, an emergency hub location or characteristic, any other hub/implant factor, or a combination thereof.

In Subset 2, the Sender ID field 106 and BAN ID field 107 are assigned within a particular range of values designated specifically for hubs that are located in doctors' offices, hospitals, or other medical facilities. Doctor's office hubs, for example, transmit wakeup or poll frames that contain Sender ID and BAN ID values within the designated medical facility range. When a node observes a medical facility value in the Sender ID and/or BAN ID fields, then the node knows that it has discovered a doctor's office or other medical facility hub. The node can then determine whether it should connect with the doctor's office hub based upon a list of designated or approved medical facility values stored on the node. If the observed Sender ID and/or BAN ID are on the node's list of designated medical facilities, then the node would connect with the doctor's office hub. However, if the hub's Sender ID and/or BAN ID values are not on the node's list of designated medical facilities, then it is likely that the discovered hub belongs to a medical facility with which the patient and implant are not registered. Therefore, it would not be power efficient for the node to connect with this unrelated medical facility hub since that hub is unlikely to be configured to monitor or support the patient's implant. The node can either return to a sleep state or may continue scanning or monitoring for a hub on its list of designated medical facilities, a home hub, or an emergency hub, if necessary.

Subset 3 comprises the remaining values of the Sender ID 106 and/or BAN ID 107 space. The Subset 3 values are applied to hubs that are set up at patients' homes or in other private locations, such as at a patient's office or workplace. When a node observes a home location value in the Sender ID and/or BAN ID fields, the node knows that it has discovered a hub that is specifically related to a particular patient. The node can then determine whether the discovered hub is its home or workplace hub based upon a list of designated or approved home values stored on the node. If the observed Sender ID and/or BAN ID are on the node's list of designated home hubs, then the node would connect with the home hub. However, if the hub's Sender ID and/or BAN ID values are not on the node's list of designated home hubs, then it is likely that the discovered hub belongs to a different patient's home. Therefore, it would not be power efficient for the node to connect with this unrelated home hub since that hub is unlikely to be configured to monitor or support the patient's implant. The node can either return to a sleep state or may continue scanning or monitoring for a hub on its list of designated medical facilities, a home hub, or an emergency hub, if necessary.

The Recipient ID 105, Sender ID 106, and BAN ID 107 fields are each one byte long. Accordingly, the Sender ID and BAN ID fields are individually 8 bits long and can each represent $2^8=256$ values individually, or $2^{16}=65,526$ values if the fields are combined. It will be understood that the "subset" groups may correspond to values for the Sender ID and/or BAN ID fields individually or taken together. Additionally, it will be understood that various combinations of the Sender ID and BAN ID fields may be used to represent the "subset" groups described above or any other such hub groupings.

In one embodiment, the implant node is provided with the acceptable Sender ID and/or BAN ID values through a connection with a trusted hub. For example, the trusted hub may send the node an emergency value from Subset 1, one or more medical facility values from Subset 2 corresponding to doctors' offices that the patient wearing the implant is likely to visit, and a value from Subset 3 corresponding to the patient's home hub. The home hub may act as the trusted hub, and the patient, a doctor, or caregiver may configure the list of identifiers used by the node via the home hub. For example, the home hub may be coupled to a user interface that allows the patient to use a menu, keyboard, or other device to identify a range of acceptable identifiers for the Sender ID and BAN ID fields. The values used by the node may be dynamically configured, including modifying how values in the Sender ID and BAN ID fields are partitioned.

In some embodiments, the trusted hub may provide additional data regarding the Subsets, such as a particular ordering of the values that indicates a preferred order in which the node should connect with the hubs. For example, the values for Subset 2 may be ordered so that the node looks for a particular medical facility hub for a certain period of time before accepting other medical facility hubs for connection. This would allow a doctor to designate a hub for preferred or primary monitoring equipment, for example. The other values listed in Subset 2 may be a hub for secondary or backup monitoring equipment that is acceptable if the primary hub in the doctor's office cannot be discovered by the implant node. The node may also be implanted or manufactured with pre-configured Subset values that may or may not be further updated by a trusted hub.

In other embodiments, the trusted hub may further indicate specific days and/or times during which the node is allowed to connect with a particular hub identified in the Subset values. For example, the values for Subset 2 may indicate when the node should or is allowed to connect with certain medical facility hubs. A doctor's office hub may be restricted to certain office hours for connection, while a hospital hub may be unrestricted as to day or time.

The implant node will wake up as frequently as appropriate to receive connection invitation polls for a connection with a relevant hub. However, the node will transmit a response for a connection with the hub only after receiving a poll with the Sender ID and/or BAN ID fields set to one of the values that were pre-configured manually or provided by the trusted hub. If the implant node receives a poll from its home hub—as identified by a designated Subset 3 value for the home Sender ID and BAN ID, for example—but the node is still connected with the home hub or another hub, the node does not respond to connection invitation polls from the hub.

In another embodiment, all hubs for emergency events or for visiting patients will have the Sender ID and/or BAN ID fields in connection invitation messages set to a special value, such as "0" or any other value. The Sender ID and BAN ID fields in other messages from the hub are set to different values. The Sender ID and BAN ID fields in messages from other hubs, such as home or non-emergency hubs, are never set to that special value. All implants may be provided with this special value, which is either hardcoded at the time of manufacture or configured through a trusted hub.

An implant will wake up as frequently as appropriate to receive connection invitation polls for a needed connection with a relevant hub. However, it will transmit a request for a connection with the hub sending the invitation only after it received a poll with the Sender ID and/or BAN ID fields set to the preset special value or with a home Sender ID and/or BAN ID value. Nevertheless, if the implant is currently connected with its home hub, it will not respond to connection invitation polls from the hub.

It will be understood that the MAC frame construction illustrated in FIG. 1 represents just one embodiment and that other identification field configurations may be used in other embodiments. For example, instead of using separate Sender ID and BAN ID fields, the frame may include a single Hub ID or HID field that identifies the hub. The HID field can be used in the same manner as described above for the Sender ID and BAN ID fields to represent different hub types or Subsets. In other embodiments, the Subset value may have a length other than one or two bytes, and a different field in the MAC frame structure (i.e., other than hub identifier fields) may be used to represent Subset values or hub types.

FIG. 2 is a flowchart illustrating a process for implementing one embodiment of the invention. In step 201, the node is provided with a list of preferred IDs for hubs in the patient's home and doctors' offices and for emergency hubs. The preferred IDs may correspond, for example, to Sender ID and BAN ID fields in a MAC frame. In step 202, the node listens to connection invitation polls. A hub may send the connection invitation polls periodically every $T_{cycle}$ seconds. Prior to step 202, the node may enter a sleep state to conserve power. The node then wakes up from the sleep state, turns on its receiver, and listens for the connection invitation polls.

In step 203, the node determines whether a connection invitation poll has been received. If no poll has been received, then the process returns to step 202 and the node continues to listen for a connection invitation poll. If a poll is received at step 203, then the process moves to step 204 where the node compares the received ID in the connection invitation poll to the list of preferred IDs provided in step 201. If the received ID is not on the preferred list, then the process returns to step 202 and the node continues to listen for a connection invitation poll.

If, in step 204, the node determines that the ID in the received connection invitation poll message is on the preferred list, then the process moves to step 205 where the node determines whether the received ID corresponds to the home ID. The home ID may be provided as an acceptable Sender ID and/or BAN ID value in Subset 3 as described above. If the received ID does not match the home ID, then the process moves to step 206 where the node responds to the hub sending the connection invitation poll.

If on the other hand, the received ID does match the home ID, then the process moves to step 207 where the node determines whether it is currently connected with the hub that sent the connection invitation poll. If the node determines that it is connected with the hub that sent the poll, then the process returns to step 202 and the node continues to listen for additional connection invitation polls. If the node determines in step 207 that it is not connected with the hub that sent the poll, then the process moves to step 206 where the node responds to the hub sending the connection invitation poll. The response to the hub in step 206 may include, for example, completing a security association process between the node and the hub.

FIG. 3 is a block diagram of an exemplary embodiment of a device 300 implementing embodiments of the invention. Device 300 may be used as a node and/or a hub/controller. In one embodiment, device 300 is a hub, gateway, or controller controlling and communicating with one or more nodes 300. Processor 301 processes data transmitted to or received from a hub or other nodes via transceiver 302 and antenna 303 and/or, in the case of a hub, via wireline interface 304 coupled to Internet or another network 305. Where device 300 is a medical implant device, wireline connection may not be present or may be unused unless the device is accessible externally. Processor 301 may be a software, firmware, or hardware based component, or a combination thereof. Processor 301 may also control the transmission and reception of frames with a hub or connected and unconnected nodes.

Memory 306 may be used to store data and computer program instructions, software and firmware used by processor 301, and any other parameters needed in the course of communication described in the above. It will be understood that memory 306 may be any applicable storage device, such as a fixed or removable RAM, ROM, flash memory, or disc drive that is separate from or integral to processor 301. Device 300 may be coupled to other devices, such as user interface 307, sensors 308, or other devices or equipment 309.

Device 300 may be adapted to operate in a body area network either as a node or as a hub controlling a plurality of nodes. Sensors 308 may be used, for example, to monitor vital patient data, such as body temperature, heart rate, and respiration. Equipment 309 may be, for example, a monitor or other device that receives and analyzes signals, such as a patient's temperature, heart rate, and respiration, from another node. Alternatively, equipment 309 may be a device for providing a service to a patient, such as controlling an intravenous drip, respirator, or pacemaker.

It will be understood that the device 300 in FIG. 3 are presented for illustrative purposes only and are not intended to limit the scope of the systems or devices that are capable of employing the hub identification and discrimination procedures described herein.

Many modifications and other embodiments of the invention will come to mind to one skilled in the art to which this invention pertains having the benefit of the teachings presented in the foregoing descriptions, and the associated drawings. Therefore, it is to be understood that the invention is not to be limited to the specific embodiments disclosed. Although specific terms are employed herein, they are used in a generic and descriptive sense only and not for purposes of limitation.

What is claimed is:

1. A method, comprising:
   receiving, by a network node from a hub, a poll message including a hub identification representing a service available near the hub;
   determining, by the network node, a condition associated with a user of the network node;
   responding, by the network node, to the poll message if the condition corresponds to the service represented by the hub identification; and
   ignoring, by the network node, the poll message if the condition does not corresponds to the service represented by the hub identification.

2. The method of claim 1, wherein, the hub identification includes an identifier selected from a group consisting of a emergency hub identifier, a medical facility identifier, or a home hub identifier.

3. The method of claim 1, further comprising:
   monitoring, by the network node, a second poll message from a second hub, if the condition does not corresponds to the service represented by the hub identification of the hub.

4. The method of claim 1, further comprising:
   extracting information from a body area network identification field in the poll message, wherein the information comprises the hub identification.

5. The method of claim 1, further comprising:
   extracting information from a sender identification field and from a body area network field in the poll message, wherein the information comprises the hub identification.

6. The method of claim 1, wherein the condition includes a medical condition selected from a group consisting of a medical emergency condition and a medical non-emergency condition.

* * * * *